US007525102B1

(12) United States Patent
Henshaw et al.

(10) Patent No.: US 7,525,102 B1
(45) Date of Patent: Apr. 28, 2009

(54) AGENT DETECTION IN THE PRESENCE OF BACKGROUND CLUTTER

(75) Inventors: Philip D. Henshaw, Carlisle, MA (US); Pierre C. Trepagnier, Medford, MA (US)

(73) Assignee: Sparta, Inc., Billerica, MA (US)

( * ) Notice: Subject to any disclaimer, the term of this patent is extended or adjusted under 35 U.S.C. 154(b) by 368 days.

(21) Appl. No.: 11/541,935

(22) Filed: Oct. 2, 2006

Related U.S. Application Data (60) Provisional application No. 60/723,985, filed on Oct. 3, 2005.

(51) Int. Cl.
*G01J 3/28* (2006.01)
(52) U.S. Cl. .................. 250/393; 250/458.1; 250/459.1
(58) Field of Classification Search .................. 250/393, 250/458.1, 459.1
See application file for complete search history.

(56) References Cited

U.S. PATENT DOCUMENTS

| 5,760,406 | A | 6/1998 | Powers |
| 5,968,766 | A | 10/1999 | Powers |
| 6,194,731 | B1 | 2/2001 | Jeys et al. |
| 6,750,006 | B2 | 6/2004 | Powers et al. |
| 2004/0175294 | A1* | 9/2004 | Ellison et al. .............. 422/68.1 |

OTHER PUBLICATIONS

Manolakis, et al., "Hyperspectral Image Processing for Automatic Target Detection Applications," Lincoln Laboratory Journal 14 (2003) pp. 79-115.
Keshava, "A Survey of Spectral Unmixing Algorithms," Lincoln Laboratory Journal 14 (2003) pp. 55-77.
Primerman, "Detection of Biological Agents," Lincoln Laboratory vol. 12 (2000) pp. 3-31.
Jeys, "Aerosol Triggers," New England Bioterrorism Preparedness Workshop (Apr. 3-4, 2002).
Lakowicz, "Principles of Fluorescence Spectroscopy," (Kluwer, New York) 1999, pp. 118-126.
Sharaf, et al., Chemometrics, pp. 155-159 (Wiley & Sons, New York) 1986.
"Laser-Induced Breakdown Spectroscopy," Applied Optics (feature issue) Oct. 20, 2003.
Existing and Potential Standoff Explosives Detection Techniques, National Research Council (The National Academies Press, Washington DC) 2004, pp. 35-55 and 71-96.

(Continued)

*Primary Examiner*—David P Porta
*Assistant Examiner*—Mark R Gaworecki
(74) *Attorney, Agent, or Firm*—Nutter McClennen & Fish LLP; Thomas J. Engellenner; Reza Mollaaghababa (57) ABSTRACT

The present invention generally provides systems and methods for detection of agents of interest in a bulk quantity of matter, which also contains clutter and other constituents that typically interfere with the detection of one or more agents of interest. A detection system of the invention generally contains a collection subsystem for obtaining a bulk sample, an interrogation subsystem for generating one or more analytical signals representative of the composition of the bulk sample, and an analytical subsystem according to the teachings of the invention that implements the methods and algorithms of the invention for analyzing the sample analytical signals to determine whether one or more agents of interest are present, e.g., at quantities above a certain threshold, in the bulk sample.

18 Claims, 7 Drawing Sheets

OTHER PUBLICATIONS

Trepagnier, et al., "Principal Component Analysis Incorporating Excitation, Emission, and Lifetime Data of Fluorescent Bio-Aerosols," PhAST Conference, Long Beach CA, May 22-25, 2006.

Henshaw, et al., "Background Suppression and Agent Detection in Multi-Dimensional Spaces," PhAST Conference, Long Beach, CA, May 22-25, 2006.

Kwan, et al., "A Novel Approach for Spectral Unmixing, Classification, and Concentration Estimation of Chemical and Biological Agents," IEEE Trans. Geoscience Remote Sensing 44 (Feb. 2006) pp. 409-419.

* cited by examiner

AGENT DETECTION IN THE PRESENCE OF BACKGROUND CLUTTER

RELATED APPLICATION

The present application claims priority to provisional application No. 60/723,985 entitled "Agent detection in the presence of background clutter," filed on Oct. 3, 2005, which is herein incorporated by reference.

This invention was made with U.S. Government support under contract number DAAD13-03-C-0077 awarded by the Department of Defense. The government has certain rights in the invention.

BACKGROUND OF THE INVENTION

The present invention relates generally to methods and systems for detecting agents in a bulk sample that can include one or more background constituents, and more particularly, for detecting bio-aerosol warfare agents.

The detection of bio-aerosol warfare agents in the presence of either indoor or outdoor backgrounds is a difficult problem. Natural backgrounds are variable and can simultaneously include multiple constituents. The variation of each constituent may be larger than the concentration level of an agent whose detection is desired. The detection problems can be further exacerbated by the presence of spikes in measurement data of a naturally-occurring background, which may be an order of magnitude larger than the contribution of the normal quiescent background. Such spikes may last for minutes and may exhibit large variations in particle count.

The detection of other important agents share some of the difficulties associated with the detection of bioaerosols. For example, chemical warfare agents may need to be detected in the presence of industrial cleaners or insecticides. Nuclear materials may be hidden by background radiation from rocks and cements, as well as by residual radiation from medical treatment or radiation from shipments of medical equipment. Signatures of explosives traces can be mimicked by foods preserved with nitrates as well as by legitimate shipments of fertilizers. Detection of pollutants and contaminants share the same problems as detection of biological, chemical, and radiological warfare agents. A solution to all of these problems requires the ability to detect low levels of agents in an ambient environment. The detection sensitivity can be increased by concentrating the sample to be analyzed, but at the risk of having both large amounts of background and small amounts of agent in the same sample. Further, simulants for a variety of agents, such as those mentioned above, are often used for detector development and testing. Thus, the detection of simulants is also an important problem requiring solution.

Some workers in the field have attempted to solve the problem of detecting low levels of agents against an ambient background by finding signatures that are unique to the agents whose detection is desired. This normally requires that signatures of agents and background constituents be unique and non-overlapping. This approach may work with signatures that have many very narrow features, such as those typically exhibited by LIBS (Laser Induced Breakdown Spectroscopy), Raman spectra, and FTIR (Fourier Transform Infrared) spectra. However, it is not suitable for signatures that have broad features, such as UV-induced fluorescence spectra and lifetime measurements, x-ray fluorescence spectra, and terahertz (THz) spectra. Hence, this conventional approach has the disadvantage that it limits the detection techniques that can be used to solve a given agent detection problem.

Another conventional method for detecting agents utilizes single particle flow-through systems, such as BAWS (Biological-Agent Warning Sensor) to make a small number of simultaneous measurements, a single particle at a time. Each particle could be classified based on this small number of measurements, and a histogram of particle locations in measurement space could be built up over time.

However, single particle flow-through systems have several disadvantages. First, the signal from a single particle is small. Expensive hardware, such as large collection optics or more powerful lasers to excite a larger return signal, can be used to compensate for this low sensitivity. However, even with more expensive hardware, the detection rate for very small particles is generally negligible, leading to an inability to detect aerosols composed of small particles (such as viruses), even if the particle number density is large. Even for large particles, a low detection rate can render sufficient data collection for a statistically meaningful detection (build-up of a particle count that is sufficient for agent detection) cumbersome and time-consuming. Second, only a small number of measurements can be made simultaneously. A small number of measurements implies a small number of histogram bins. This can result, in turn, in placing different particle types in the same histogram bin, leading to a high false alarm rate. Finally, the flow of particles near the large aperture collection optics of such systems can lead to fouling of the optics, thus lowering the optical efficiency of the system and driving up maintenance costs.

Accordingly, there is a need for enhanced methods and systems for detecting agents in a variety of backgrounds.

SUMMARY OF THE INVENTION

The agent-detection methods of the present invention can be utilized in conjunction with bulk collection and immobilization of a sample under investigation to achieve greater sensitivity, lower cost than conventional techniques, and to render a large variety of measurements of the sample feasible. As discussed in more detail below, the methods and systems of the invention allow suppressing contributions of unwanted background constituents in a bulk sample to information obtained about the sample (e.g., via spectral measurements) by utilizing previously-obtained information about the signatures of the agents and the background constituents of interest. The present invention advantageously increases the types of signatures that can be employed for agent detection.

In one aspect, the invention provides a method of detecting an agent in a bulk sample, which includes at least one background constituent, that comprises utilizing a measurement modality to interrogate the sample with electromagnetic radiation so as to generate spectral data corresponding to the sample. The principal components of the spectral data can then be derived and represented as a vector in a principal component space. A rotate-and-suppress transformation can be applied to the principal component vector, wherein the transformation suppresses, and preferably eliminates, the contributions of the background constituent, if present, thereby generating a background-suppressed principal component vector corresponding to the sample. This transformed sample vector can be compared with a background-suppressed principal component vector corresponding to the agent to determine whether the agent is present in the bulk sample. The background-suppressed principal component vector of the agent can be generated by application of the rotate-and-suppress transformation to the principal components of the spectral data of the agent obtained by employing the same measurement modality as that utilized to interrogate the sample.

The above step of comparing the background-suppressed principal component vectors of the sample and the agent can comprise determining a spectral angle that separates the two vectors in the principal component space. If the spectral angle is within a pre-defined range, a detection of the agent in the sample can be indicated. In some embodiments, this criterion constitutes only one prong of a two-prong test for indicating the detection of the agent within the sample. The other prong requires that the dot product of the two vectors obtained, for example, in selected two-dimensional sub-spaces of the principal component space, be above a pre-defined threshold. In some embodiments, once it is determined that the angle between the two vectors lies in a predefined range, a warning is issued. If not only the angle is within the range, but also the dot product is above a selected threshold, an Alert/Alarm processor is triggered. Such a two-step test procedure can lower the risk of issuing false alarms.

In a related aspect, the same measurement modality as that utilized for obtaining the agent and the sample spectral data is employed to generate spectral data corresponding to the background constituent. The principal components of the background spectral data are then derived and represented as a vector in the principal component space. The following two transformations of the principal component vector are then combined to form the aforementioned rotate-and-suppress transformation. First, the principal component vector is rotated so as to be aligned along an axis of the principal component space (that is, it is rotated so as to include only one component). Subsequently, the dimension of the principal component space corresponding to that axis is eliminated. In other words, the remaining component of the rotated vector is eliminated. The combination of these two transformations generates the rotate-and-suppress transformation.

As will be discussed, this method is equivalent to simply projecting into a subspace along the background vector, so that the vector is along an axis for computational convenience.

In many embodiments, Principal Component Analysis (PCA) is utilized for deriving the principal components of spectral data associated with the agents, background constituents, as well as the samples under investigation. Principal Component Analysis (PCA) is a well-known technique for determining the most important components of multi-dimensional measurements of a collection of agents and backgrounds. Using PCA, the dimensionality of the measurement space can be reduced while maintaining the distinguishing features of the original measurements.

Typically, the principal components for varying concentrations of a given agent or background will form a straight line in principal component space pointing toward the origin. The origin is the location of the signature of the measurement apparatus in the principal component space in the absence of any agent or background. The straight line for each agent makes an angle with other agents or background constituents. This "spectral angle" can be defined for any number of principal component dimensions. As the number of dimensions increases, the spectral angle between randomly chosen vectors tends toward 900.

In many embodiments of an agent-detection method of the invention, the method begins by rotating the principal component (PC) space to place the major background constituent normally seen at the sample collection location into a single component in PC space. Projection into a new PC space orthogonal to the major background constituent is achieved by simply dropping that component axis. The result is suppression of variations of that background constituent but with loss of one dimension. The process can be repeated for each background constituent that is larger than a desired level of detection of the agent(s) of interest, as long as there are remaining dimensions that can be discarded. The agent library is rotated and projected in the same manner as the sample. As noted above, the agent detection is determined by requiring that the sample (the background-suppressed sample vector in the principal component space) be within a small spectral angle of an agent (the background-suppressed agent vector in the principal component space), and that the dot product of the sample and agent vectors simultaneously exceed a threshold determined by the level of detection desired. False alarms can be reduced, at the expense of response time, by requiring successive detections to declare an alarm. We refer to this successive detections requirement as "Alert/Alarm" processing.

A variety of measurement modalities can be employed in agent-detection methods and systems of the invention. Some of these measurement modalities include, without limitation, fluorescence excitation-emission spectroscopy (e.g., UV-induced fluorescence excitation-emission spectroscopy), fluorescence life-time spectroscopy (e.g., UV fluorescence decay time histories), X-ray fluorescence spectroscopy, laser-induced breakdown spectroscopy, Raman spectroscopy, Terahertz transmission or reflection spectroscopy, hyperspectral imaging, and performing optical reflectance or scattering measurements. Agent and background measurements can be made with the same or similar instruments as those utilized to collect samples for detection of agent(s) therein, or can be made with different instruments. Alternatively, the methods of the invention can be applied to data collected and disseminated by third parties. Further, as discussed below, measurements corresponding to background constituents can be obtained separately or can be determined by techniques such as end-member analysis.

Further, the methods and systems of the invention can applied to and utilized with a variety of sample collection modalities. For example, these methods can be utilized to interrogate an ambient volume of air or a fluid, or interrogate a sample collected and concentrated into a fluid, or interrogate a sample collected onto a substrate.

In another aspect, a method of the invention for detecting an agent in a bulk sample having at least one background constituent includes utilizing a plurality of (e.g., two) measurement modalities to interrogate the sample with electromagnetic radiation so as to generate a plurality of sets of spectral data, each of which corresponds to one of those measurement modalities. The sets of the spectral data are combined into a composite data vector (herein also referred to as feature vector), and that vector is transformed into a principal component vector comprising the principal components of the data. The principal component vector is then transformed, e.g., via application of a rotate-and-suppress transformation thereto, so as to generate a transformed principal component vector. The transformation suppresses, and preferably eliminates, the contribution of the background constituent, if present. The transformed principal component vector can then be compared with a background-suppressed principal component agent vector (a principal component vector corresponding to the agent to which a rotate-and-suppress transformation has been applied) to determine whether that agent is present in the sample in a quantity that would warrant indicating detection.

In a related aspect, in the above detection method, one or more of the data sets are normalized prior to combining them into a single data vector. In some embodiments, one of the measurement modalities comprises fluorescence excitation-emission spectroscopy and another comprises fluorescence life-time spectroscopy.

In some embodiments of the invention, by stringing together the excitation-emission spectra and the lifetime measurements in a suitable weighted vector, as discussed in more detail below, the principal components can be calculated by applying a matrix transformation to the vector.

In other aspects, the invention provides systems for detecting agent(s) in a bulk sample. One such system can include a spectrofluorometer with a lifetime measurement option that includes modules for implementing the above analysis methods of the invention. For example, such a system can include a background library for storing data corresponding to at least one background constituent, and an agent library for storing principal components of measurement data corresponding to the agent. The system can further include a preprocessing module in communication with the libraries and adapted to receive measurement data corresponding to a test sample. The module calculates a rotate-and-suppress transformation and applies that transformation to measurement data corresponding to the test sample so as to generate transformed principal component vectors corresponding to the test sample. The transformation suppresses the contribution of the background constituent, if present. Further, the preprocessing module applies the rotate-and-suppress transformation to principal component vectors corresponding to the agent. An agent detection module, which is in communication with the preprocessing module, receives the transformed principal component vectors corresponding to the sample and the agent, and compares those vectors to determine whether the agent is present in the sample.

Further understanding of the invention can be obtained by reference to the following detailed description, in conjunction with the associated figures, described briefly below.

BRIEF DESCRIPTION OF THE DRAWINGS

FIG. 1B is a schematic diagram of a system according to one embodiment of the invention for implementing the method of FIG. 1A, FIG. 2 schematically illustrates two different types of measurements and a method for weighting and combining these measurements into a single feature vector, FIG. 3 graphically illustrates that the principal component vectors of a specific agent or background constituent at different concentrations (with the zero concentration at the origin) in a background-subtracted PC space, indicating that the vectors form a straight line through the origin, FIG. 4 schematically depicts the suppression of a single background constituent by rotation and projection transformation according to the teachings of the invention (the resulting PC space has one less dimension than the space before the rotation and projection), FIG. 5 depicts a geometric interpretation of the rotate-and-suppress method for suppressing a background constituent, FIG. 6 schematically depicts criteria for indicating detection of an agent based on a spectral angle separating a test sample's background-suppressed PC vector from a respective vector of the agent and a predefined threshold, and FIG. 7 schematically depicts an apparatus for performing fluorescence excitation-emission and lifetime spectroscopy.

DETAILED DESCRIPTION

The present invention provides generally methods and systems for detecting an agent in a sample under investigation in the presence of background clutter (e.g., in the presence of interfering background constituents). An agent detection method according to the teachings of the invention can suppress the contributions of one or more background constituents to spectral data obtained from the sample so as to facilitate detection of an agent in that sample. The agents of interest can be, without limitation, bio-warfare agents, chemical warfare agents, radiological agents, explosives, or pollutants (e.g., heavy metals). As discussed in more detail below, a detection method of the invention is capable of suppressing contributions from multiple, independent background constituents to measured data obtained from a sample. Further, a background suppression and detection method of the invention can adapt to the background in any location or season, and can suppress both the normal quiescent contributions of a background as well as those contributions that are manifested as large, variable spikes. In many embodiments discussed below the teachings of the invention are illustrated through their application to excitation-emission spectra and time histories (lifetime) of UV-induced fluorescence. It should, however, be understood that these teachings are equally applicable to any detection problem where a large number of measurements of agents, backgrounds and samples to be tested can be made.

Figure 1A:
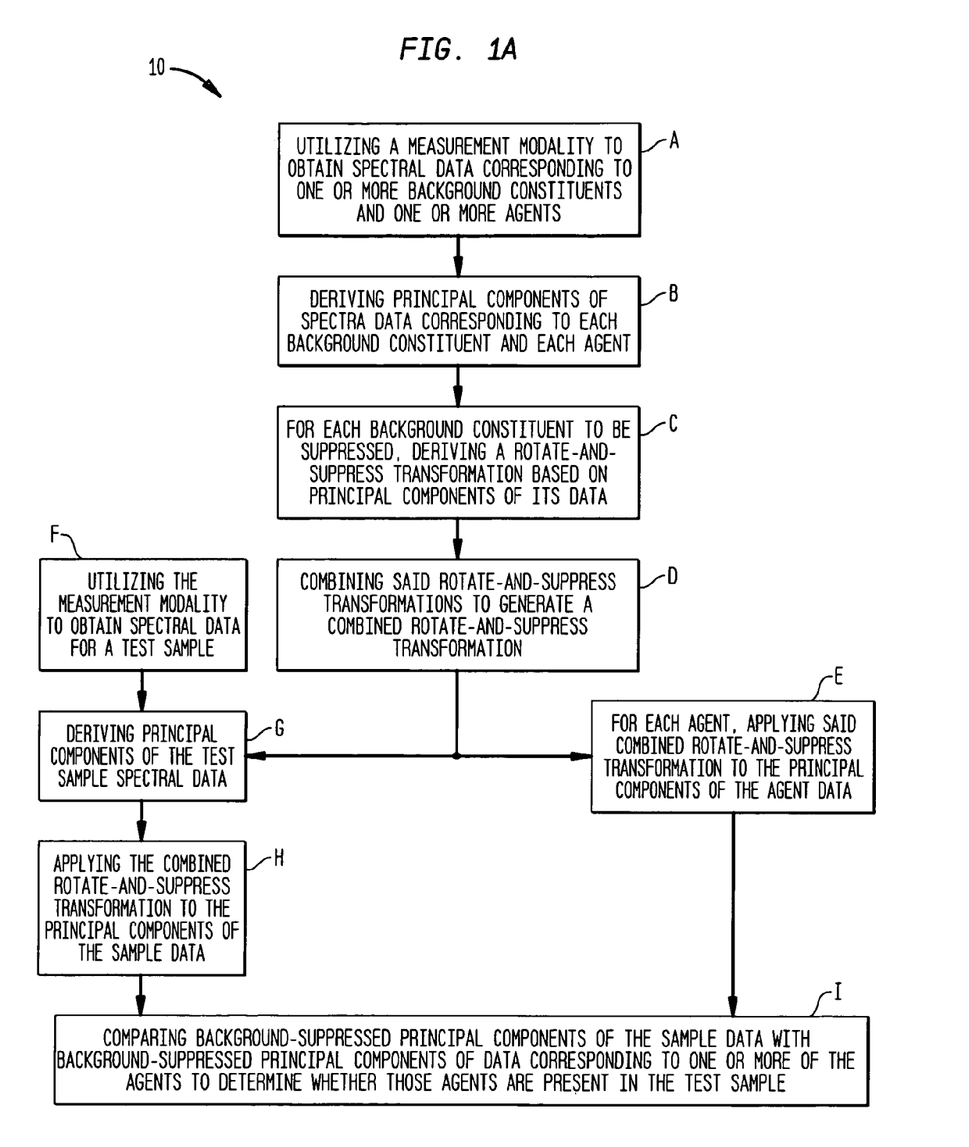
FIG. 1A is a flow chart depicting various steps of an exemplary embodiment of a method of the invention for detecting agents in the presence of background clutter.

With reference to a flow chart 10 of FIG. 1A, an exemplary embodiment of a detection method of the invention can include obtaining measurements of samples of ambient background constituents (i.e., a background in which the detection of an agent is desired) as well as those of one or more agents of interest (step A). In many embodiments, these measurements comprise interrogating the background constituents and the agents with electromagnetic radiation to obtain spectral data corresponding thereto.

The spectral data corresponding to each background constituent and each agent can be subjected to a Principal Component Analysis (PCA) to derive its associated principal components (step B). For each background constituent, a rotate-and-suppress transformation can derived based on its principal components that can be applied to spectral data obtained for the agent(s) or test samples of interest to suppress the contribution of that background constituent to the data (step C). These rotate-and-suppress transformations can then be combined, e.g., via multiplication of matrices representing them, to obtain a composite background-suppression transformation (step D). The rotate-and-suppress transformations can be stored in a library to be retrieved and utilized when measurements are made on test samples, in a manner discussed below.

For example, the composite background-suppression transformation can be applied to principal components of each agent, that is to the principal component vector corresponding to each agent, to generate a plurality of background-suppressed principal component agent vectors (herein also referred to as reference agent vectors) (step E).

The composite transformation for suppressing the background contributions as well as the reference agent vectors can then be utilized in the following manner to determine whether one or more of the agents are present in a test sample. A test sample can be interrogated by employing the same measurement modality as that utilized for collecting data for the background constituents and the agents so as to generate spectral data corresponding to that test sample (step F). The spectral data can then be transformed into the principal component space (step G). For example, the spectral data can be subjected to a PCA analysis so as to generate its principal components, which can be represented as a vector in the principal component space.

The aforementioned composite background rotate-and-suppress transformation can then be applied to the principal component vector of the test sample so as to suppress contributions from the background constituents thereto (step H). The application of the background rotate-and-suppress transformation to the sample's principal component vector results in generating a background-suppressed principal component vector corresponding to the test sample. That background-suppressed principal component vector can then be compared with any of the background-suppressed PC agent vectors to determine whether that agent is present in the test sample (step I). For example, the presence of an agent in the test sample can be established if an angle between the test sample's background-suppressed principal component vector and a background-suppressed PC agent vector lies within a predefined range and the dot product of the two vectors exceeds a predefined threshold.

Figure 1B:
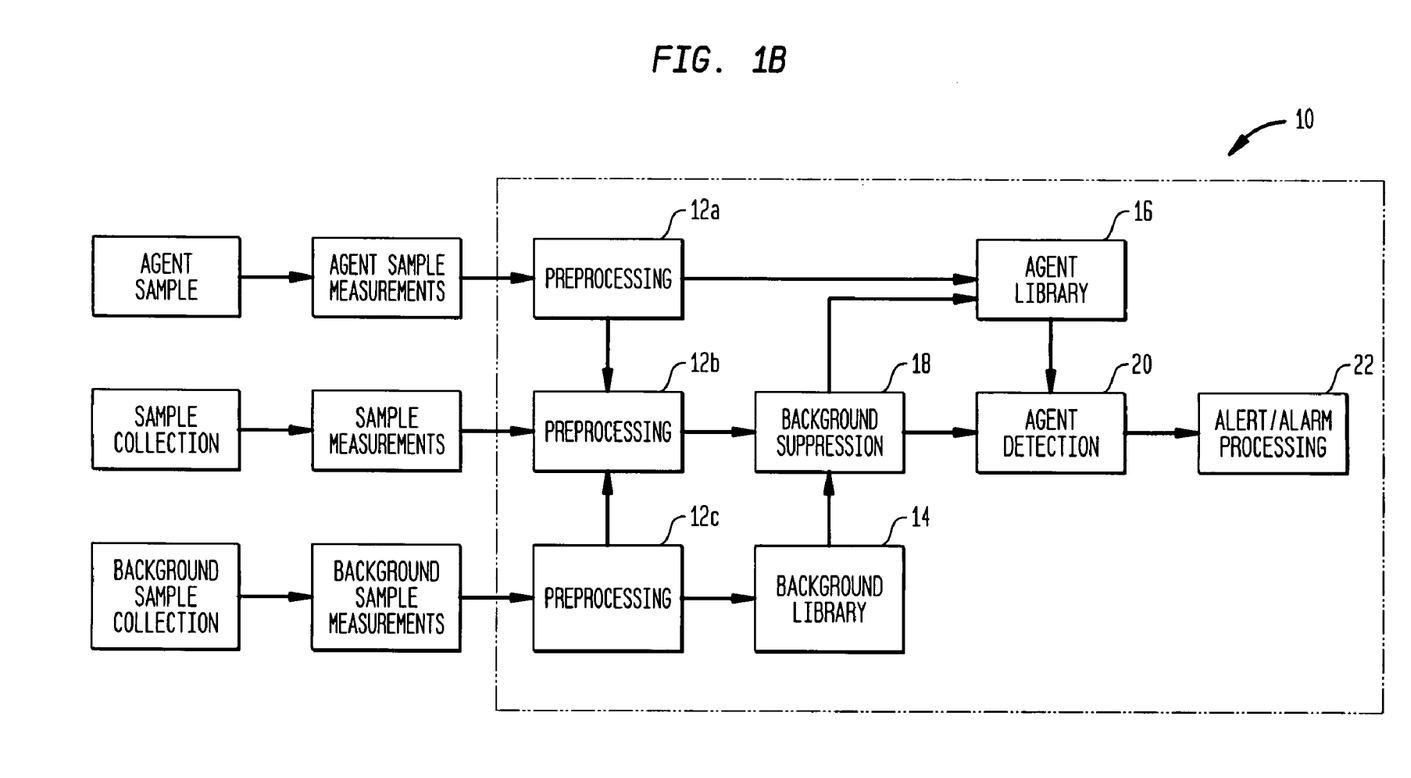

FIG. 1B schematically depicts an exemplary system according to one embodiment of the invention that implements the above method for detecting agent(s) of interest in the presence of background clutter. The system 10 includes preprocessing modules 12a, 12b, 12c that receive, respectively, measurement data corresponding to one or more agents of interest (A), measurement data for a sample under investigation (S) and measurement data for one or more background constituents (B). Each preprocessing module generates the principal components of the data it receives. Typically, the principal component transformation applied to each of the data streams will be identical. Although the preprocessing modules are shown as separate entities, in some embodiments they can constitute a single logical entity that can perform the functionality of the three.

Further the preprocessor 12c generates background principal components and communicates these to a background library 14 for storage therein. The preprocessor 12a, in turn, transmits the principal components of the agents of interest to an agent library 16 for storage. These libraries are then utilized in a manner discussed below to analyze data obtained from a test sample for detection of one or more of the agents corresponding to those in the agent library.

More specifically, the preprocessor 12b communicates the principal components of the data obtained for a sample under investigation to a background suppression module 18. The background suppression module 18, in turn, retrieves the background constituents (data corresponding to these constituents) from the background library 14, calculates the respective rotate and suppress transformations, and applies these transformations to the principal components of the test sample data, as well as the principal components of one or more agents of interest, retrieved from the agent library. An agent detection module 20 then receives the background-suppressed principal component vectors corresponding to the test sample and the agents of interest and compares these vectors in a manner discussed above to determine whether one or more agents of interest are present in the sample. Upon establishing detection of one or more agents, the agent detection module can trigger an alert/alarm processing unit 22 to issue an alert/alarm.

In many embodiments, the agent and the background libraries are compiled prior to obtaining and/or analyzing measurement data corresponding to a sample under investigation. In other embodiments, the compilation of the libraries and obtaining and/or analyzing the sample's measurement data can be performed concurrently.

In one embodiment of the invention, fluorescence EXcitation-EMission spectra and fluorescence Lifetime data are captured for agents, backgrounds and real-time test samples. These data are herein referred to as XML measurements. Other types of measurements can include, without limitation, optical reflectance or scattering measurements, x-ray fluorescence spectra, laser-induced breakdown spectroscopy (LIBS) spectra, Raman spectra, or Terahertz transmission or reflection spectra. XML measurements can be preprocessed, e.g., prior to interrogating the test samples, to create agent and background libraries, such as those discussed above. The agent and background XML measurements can be preprocessed to combine them into a single data vector for each measurement (e.g., a single data vector corresponding to the background XML measurements and a single data vector corresponding to the agent XML measurements can be formed), and then the principal components of the set of measurements can be determined using standard methods, e.g., Principal Component Analysis (PCA).

Figure 2:
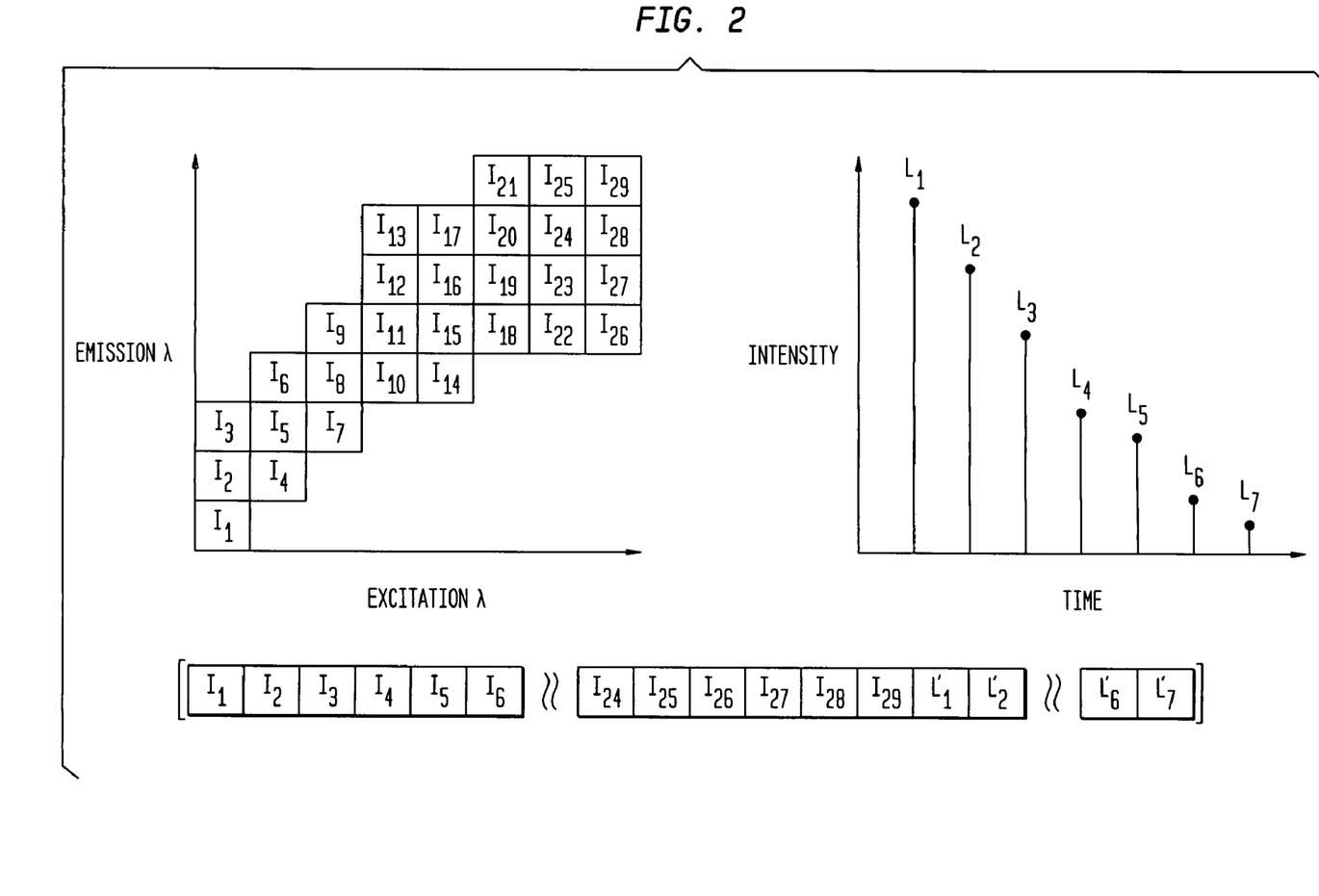

The XML measurements can be converted to a single data vector for further analysis by using, for example, the method shown schematically in FIG. 2. For example, in this exemplary embodiment, excitation-emission spectrum intensities ("$I_1$" through "$I_{29}$") are "unwrapped" column by column into a single vector. Time history data (lifetime measurements denoted by "$L_1$" through "$L_7$") can then be appended to that vector, but the lifetime measurements are re-normalized, as denoted by the primes in the vector at the bottom of FIG. 2. In this embodiment, the normalization is chosen so that the area under the lifetime curve is equal to the steady state intensity from the location in excitation-emission space where the lifetime measurements are taken. This normalization allows the two measurements to be combined on the same footing. The actual number of excitation-emission spectral points and time history points may vary from those shown in the figure.

Each XML measurement taken can be converted to a single data vector using the above procedure. Subsequently, a set of XML measurements that comprise, for example, measurements of different analytes (agents, simulants, or interferents) taken at different concentrations in multiple replicates, can be analyzed by utilizing Principal Component Analysis (PCA), which is a data analysis method known in the art. For example, it is described by Sharaf, et al. in Chemometrics (Wiley & Sons, New York) 1986, which is herein incorporated by reference. PCA can provide a standard eigenvector decomposition of the XML vector space, with the vectors (the "principal components") arranged in the order of their eigenvalues. There are generally far fewer meaningful principal components than nominal elements in the data vector, because neighboring fluorescent wavelengths are typically very highly correlated. The number of meaningful principal components is a measure of how many real independent variables are present in the XML space.

Figure 3:
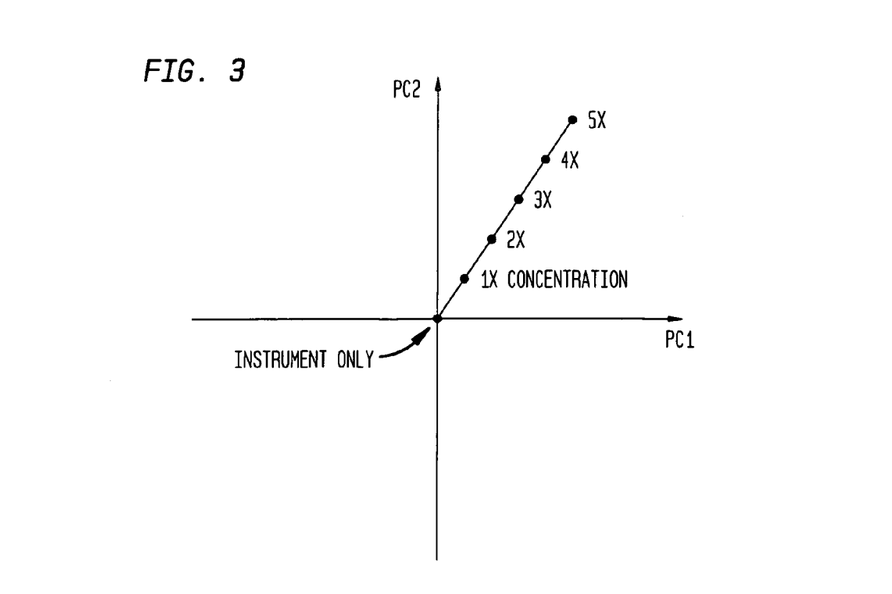

A striking result is seen when the multiple replicates at different concentrations are plotted in principal component (PC) space: each analyte forms a vector as shown in FIG. 3. When the signature of the substrate or medium containing the agent or background is subtracted from each vector, the vectors emanate from the origin and each vector's length depends on concentration of its associated analyte. This fact permits a vector-based analytical approach for detecting analytes (agents) of interest in a test sample. More specifically, each analyte has a characteristic vector, and how different one analyte is from another can be measured by how far apart their respective vectors are. Subtraction of the baseline spectrum of the substrate or medium containing the agents and backgrounds allows the use of different collection and concentration methods, including deposition onto a substrate of various materials (e.g., a metal surface or Teflon tape), collection and concentration into water or other liquid such as ethylene glycol, or interrogation of a large volume of air or water containing unconcentrated agents and backgrounds.

Normally, measurements of agents will be performed in a laboratory setting for safety reasons. However, measurement data for simulants and background may be obtained in either a laboratory or ambient natural setting. Ideally, replicates of each agent, simulant, or background constituent will have been measured separately as described above. In some cases, it may be desirable to measure the background in a natural setting in which the background constituents are mixed together in independently varying amounts. In such a case, techniques well-known in the field of multispectral analysis can be used to determine the individual background constituents, typically known as "endmembers." Some examples of such techniques are described in an article entitled "A Survey of Spectral Unmixing Algorithms," by N. Keshava published in Lincoln Laboratory Journal 14 (2003), which is herein incorporated by reference. The endmembers determined from a reasonably large set of measurements can become the background library for the local ambient setting. It should be obvious that either a background library measured in a laboratory setting or a background library determined from ambient measurements can be used in the agent detection and background suppression methods of the invention.

The principal components of agents and backgrounds may have very different values; typically there are a few strong components and a larger number of weaker components. In some cases, it may be desirable to scale the axes of the principal component space for display or prior to subsequent computations. For example, the axes can be scaled so that each PC axis has the same dynamic range. This would be equivalent to autoscaling the axes in a plot. By way of example, the axes can be scaled so that measurement noise is equal on each axis. In this case, measurement noise would form a hypersphere in the PC-space following scaling.

Figure 4:
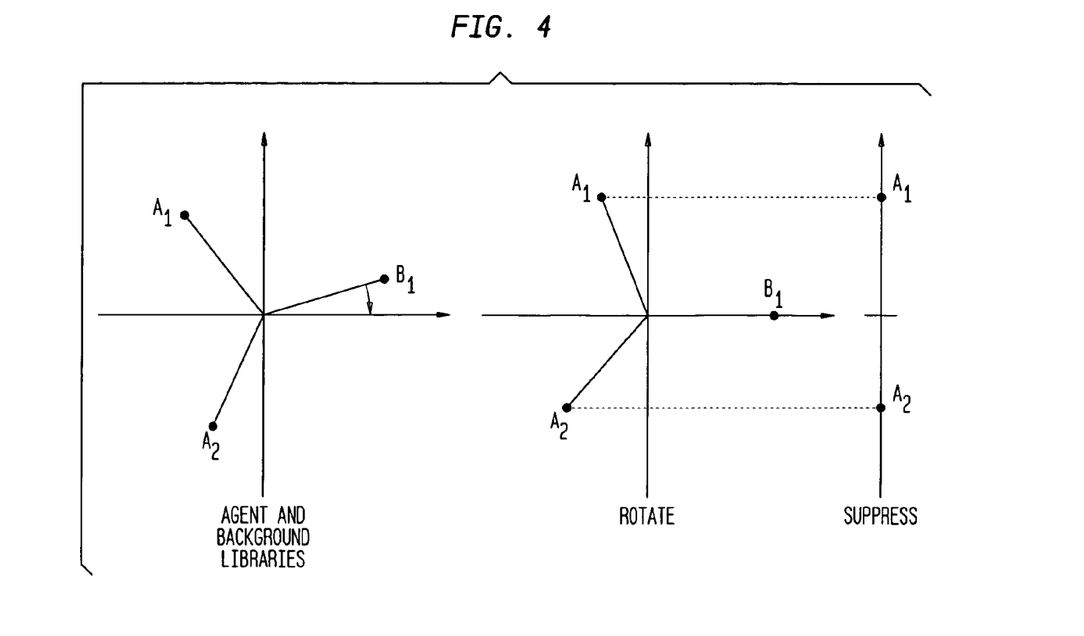

The rotate-and-suppress (RAS) method makes use of the fact that any specific background constituent forms a vector in PC-space. The method works by rotating the multidimensional PC-space so that a background constituent PC-vector is contained in a single component, then suppressing the background by dropping that component from the PC-space. By way of example and only for illustrative purposes, FIG. 4 schematically shows how RAS operates in two dimensions to suppress a single background constituent. Note in the figure that the background constituent $B_1$ is eliminated, and that in the process one dimension of the principal component space is lost. Typically, the RAS process starts operating in a much higher dimensional space, and the RAS process is applied several times in succession to eliminate multiple major background constituents. It should be noted that collection of more fluorescence data points, leading to a larger number of principal components, provides the ability to suppress a larger number of background constituents.

Figure 5:
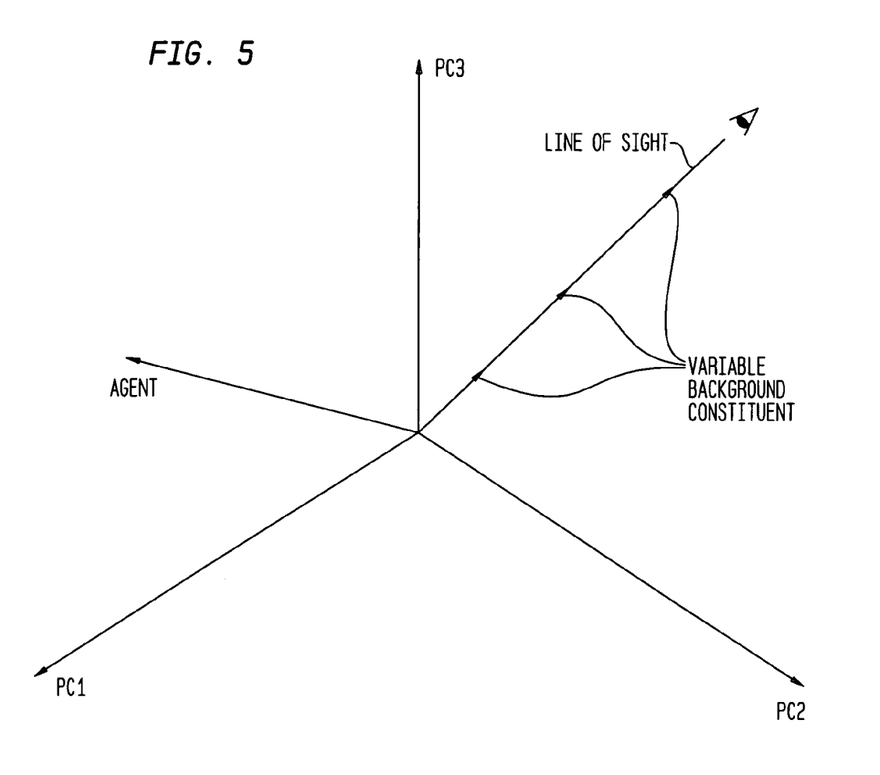

A geometric interpretation of a method of the invention will help clarify the mathematical description which follows. FIG. 5 shows a perspective view of a background constituent vector and an agent vector in 3-space. Captured data have shown that the length of the background vector varies over a very large dynamic range, with spikes of unpredictable length that can be an order of magnitude larger than the variations in the recent past. If we assume that the background constituent has been characterized so that its direction is known, the effect of these large, unpredictable variations can be almost completely eliminated. Imagine, in 3-space, that an observer positions himself so that his line of sight is exactly along the background vector. In this case, the variation in the background will be unseen by the observer. Any agent not exactly parallel to the background will have a component perpendicular to the line of sight which can be seen by the observer. Moving the observer's point of view to be along the line of sight of the background vector, and then detecting agent vectors perpendicular to this line of sight is exactly analogous to the Rotate and Suppress method to be described further below. Those having ordinary skill in the art will appreciate how to extend this geometrical argument in 3-space into higher dimensional spaces.

In general, in a method of the invention to rotate a background vector $B_1 = [B_1, B_2, \ldots B_i, B_j, \ldots B_N]$ in the principal component space (herein also referred to as principal component background vector) so as to set its $i^{th}$ component, namely, $B_i$ to zero, the following quantities are computed:

$$D = \sqrt{B_i^2 + B_j^2}$$

$$C = B_j/D$$

$$S = -B_i/D$$

The rotated background vector can then be given by:

$$B'_1 = [B_1, B_2, \ldots 0, -SB_i + CB_j \ldots B_N]$$

The rotation matrix for the rotation described above is given by:

$$R_1 = \begin{bmatrix} 1 & 0 & & & & 0 \\ 0 & 1 & & & & \\ & & \ddots & & & \\ \vdots & & & C & S & \vdots \\ & & & -S & C & \\ & & & & & \ddots \\ 0 & & \cdots & & & 1 \end{bmatrix}$$

where the diagonal elements not shown are equal to unity, and the off-diagonal elements not shown are equal to zero. The "C" entries are in elements (i,i) and (j,j) and the "S" entries are in elements (i,j) and (j,i). This method can be performed multiple times to set all but one of the background components to zero. The transformation matrices for each rotation can be combined using standard matrix multiplication techniques to compute the overall transformation.

Once there is only a single non-zero component remaining in rotated background vector $B'_1$, that component can be eliminated from all rotated library entries for both agents and background constituents. The combined rotation matrix is given by:

$$R_{C1} = R_{N-1} \times R_{N-2} \times \ldots \times R_1 = \begin{bmatrix} r_{11} & \cdots & r_{1N} \\ \vdots & & \\ r_{N1} & \cdots & r_{NN} \end{bmatrix}$$

When the combined rotation matrix is applied to the principal components of the real-time test samples and the non-zero component of the background is dropped, any contribution due to background constituent $B_1$ will be eliminated. If the row of the combined rotation matrix corresponding to the non-zero component of the background is dropped, then the resulting transformation matrix will perform the entire operation when it multiplies any set of principal components derived from agent samples, background samples, or real-time samples for testing. This transformation matrix is given by $$T_{C1} = \begin{bmatrix} r_{11} & \cdots & r_{1,N} \\ \vdots & & \vdots \\ r_{N-1,1} & \cdots & r_{N-1,N} \end{bmatrix}$$

A second background constituent can be eliminated in the same fashion. In this case, the exemplary background constituent has one fewer component:

$$B'_2 = [B_1, B_2, \ldots B_i B_j, \ldots B_{N-1}],$$

as do the resulting rotation matrices. Note that the use of the prime indicates that the components of the second background vector to be eliminated should be from the rotated background library.

The RAS rotations are determined by the agent and background libraries measured at any particular location and season. The combined rotation determined by the background library is applied to the collected samples in real time by a matrix multiplication which combines all the rotations and dropping of components into a single matrix calculated ahead of time. This combined transformation for removal of M background constituents is given by $$T_C = T_{CM} \times \ldots \times T_{C1}$$

Subsequent multiplication of the principal components derived from data (e.g., spectral data) obtained for a sample to be tested by the combined matrix $T_C$ results in the background suppression of those components. Because this operation comprises a single matrix-vector multiplication and the matrix $T_C$ can be computed ahead of time, it can be done in real-time with no significant computational burden.

Agent detection can then performed in the rotated Principal Component space (PC-space) in the following manner. PC-space with more than three dimensions can only be visualized using subspace graphs. Measurements of UV-induced fluorescence intensity at many excitation-emission wavelength pairs will provide at least seven principal components, and the addition of fluorescence lifetime information will provide at least two more dimensions. The number of principal components will likely increase as more analytes are added to the libraries. With a seven- to nine-dimensional space, a large number of subspaces need be explored to determine whether two analytes are well-separated. The Spectral Angle (SA) is a one-dimensional metric which can be used to determine the separation of agents or simulants from backgrounds.

For two multidimensional vectors a and b, the spectral angle between them is given by:

$$SA(a,b) = \cos^{-1}\left[\frac{a \cdot b}{|a||b|}\right].$$

The two vectors are aligned when the normalized dot product (the quantity in the square brackets) is equal to one. This condition is met only when the normalized components of each vector are equal. As the components become unequal (or even of opposite sign) the quantity in the brackets can approach zero, in which case the spectral angle approaches 90° and the vectors are orthogonal.

Figure 6:
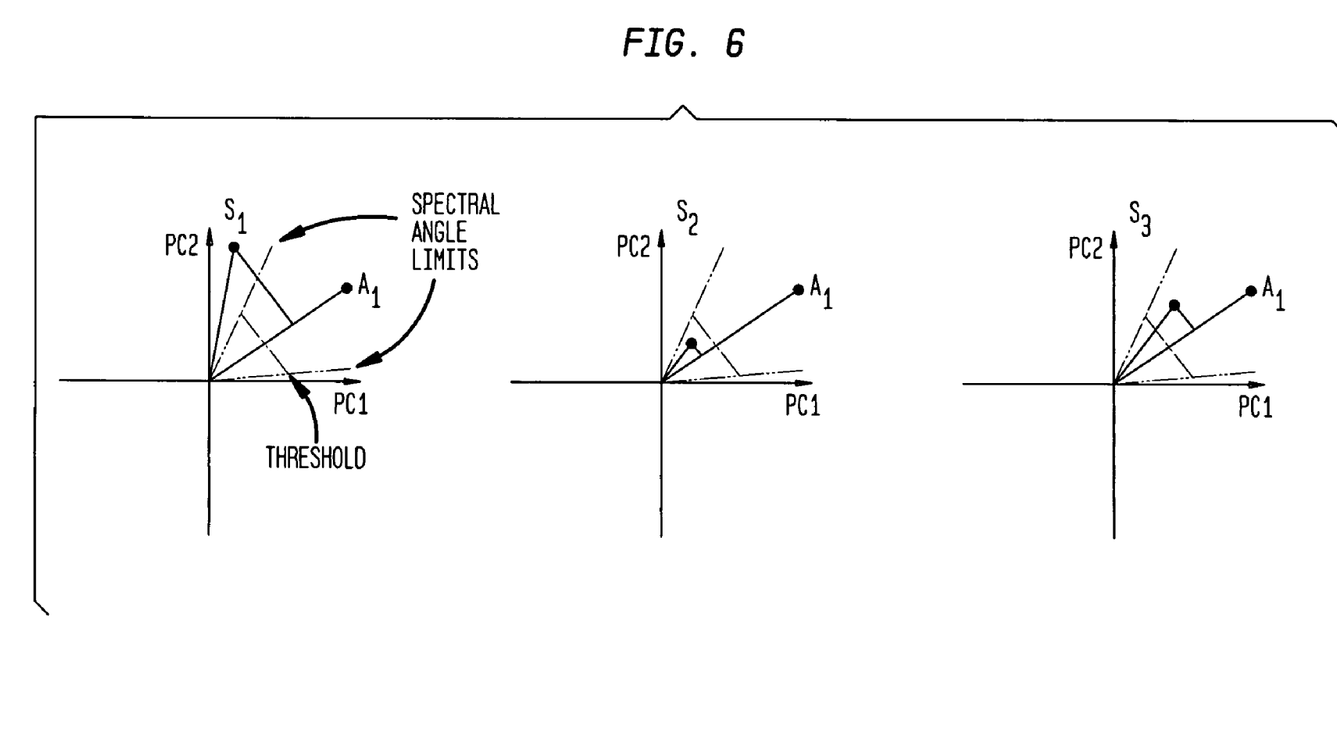

A detection method of the invention compares the background-suppressed test samples with the agents in the library to determine whether one or more of those agents are present in the test sample. Note that the agent library has been subjected to the RAS matrix transformation. FIG. 6 schematically shows the application of exemplary criteria that can be utilized for determining a match to an agent, i.e., for determining whether an agent is present in the test sample. First, a spectral angle (SA) between the background-suppressed principal component vectors corresponding to the test sample and the agent of interest is computed. If the SA is greater than a preset value (e.g., 30°) no detection occurs. If the SA is within a predefined range, e.g., the cone defined by the SA threshold shown by the dotted lines in FIG. 6, then the dot product of the sample and the agent is computed. When the dot product exceeds a second preset threshold, detection occurs. By way of example, in FIG. 6, $S_1$ (on the left) and $S_2$ (in the middle) fall outside the detection region, but $S_3$ (on the right) is a detected event.

In some embodiments, when a detection occurs, an Alert/Alarm is issued, e.g., the Alert/Alarm processor (rightmost box in FIG. 1B) is triggered. By requiring two successive detection events (Alert then Alarm) all single event detections can be eliminated, significantly reducing the probability of false alarm without affecting the probability of detection.

Figure 7:
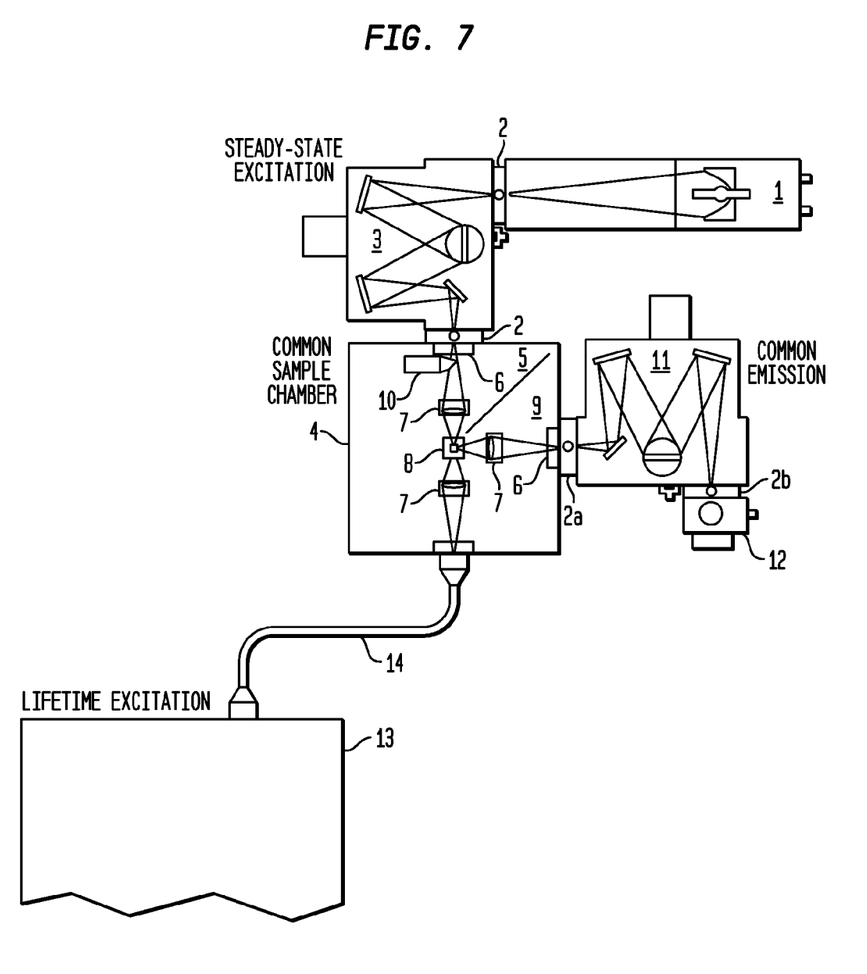

As noted above, the agent detection methods of the invention can be utilized in connection with a variety of measurement modalities, and are not limited for use with fluorescence excitation-emission and lifetime measurements. As such, they can be utilized to process data obtained from a variety of measurement devices. For example, in the above exemplary embodiment, the processing of XML measurements was discussed for illustrating the features of an exemplary embodiment of an agent detection method of the invention. An embodiment of an apparatus for gathering XML measurements is shown in FIG. 7. The exemplary apparatus includes a single sample chamber (4) serviced by both a steady-state spectrofluorometer (top of figure) and a lifetime spectrofluorometer (bottom of figure). This apparatus is available commercially from Photon Technology International, Birmingham, N.J.

In the steady-state spectrofluorometer, a Xenon lamp (1) provides illumination that is focused onto a slit (2) and thence enters an excitation monochromator (3). It then enters a second slit (2) that defines the wavelength spread, and into a sample chamber (4). The wavelength-selected excitation light is focused via optics (7) onto a cuvette, which holds a sample of interest (not shown), and is held in a cuvette holder (8). Fluorescence radiation (9), emitted by the sample in response to the excitation light, is then focused onto slit (2a) and enters an emission monochromator (11). Passing through the emission monochromator, emission radiation in the selected waveband is focused onto another slit (2b) and enters a photomultiplier tube (12), where the steady-state intensity of the selected emission waveband from the selected excitation is detected.

In the lifetime spectrofluorometer, shown at the bottom of the drawing, the Xenon arc lamp from the steady-state system is replaced by a short pulse of light delivered by a laser (13). The arrival of the light pulse is delayed by the fiber optic (14) for a sufficiently long time to enable gating electronics (not shown) to set up a moving time gate on the photomultiplier tube output relative to the excitation pulse. Subsequent to the laser light pulse arrival, fluorescence photons are emitted by the sample and pass through the same emission path as before and strike the photomultiplier. The time gate which moves relative to the arrival of the excitation pulse enables the decay of fluorescence output relative to excitation to be directly measured.

The fluorescence excitation-emission data as well as fluorescence lifetime data generated by the above apparatus can then be analyzed in a manner discussed above to determine whether one or more agents of interest are present in the sample under investigation.

To further illustrate the salient features of agent detection methods of the invention, the following hypothetical example is provided. It should be understood that the example is provided only for illustrative purposes and is not intended to necessarily indicate the dimensionality of the data vectors or that of the principal component space.

EXAMPLE

A simple numerical example will further illustrate the operation of the Rotate and Suppress method according to the teachings of the invention. In this example, the agent and background vectors are defined in three-dimensional space, and the suppression of the background vector results in a two-dimensional space. Assume that the Principal Components of a background constituent and two agents of interest are specified by:

$B_1 = [3,4,5]$ $A_1 = [1,0,2]$ $A_2 = [1,2,0]$

Application of the first rotation results in setting the first component of $B_1$ to zero. More specifically, the following rotation matrix rotates all of the first component of the background into the second component:

$$R_1 = \begin{bmatrix} 4/5 & -3/5 & 0 \\ 3/5 & 4/5 & 0 \\ 0 & 0 & 1 \end{bmatrix}$$

and the resulting rotated background vector is given by:

$$B_1' \times R_1 \times B_1^T = \begin{bmatrix} 0 \\ 5 \\ 5 \end{bmatrix}.$$

In the second rotation, the second component of $B'_1$ is set to zero, without reinserting any signal into the first component. This second rotation matrix is given by:

$$R_2 = \begin{bmatrix} 1 & 0 & 0 \\ 0 & \sqrt{2}/2 & -\sqrt{2}/2 \\ 0 & \sqrt{2}/2 & \sqrt{2}/2 \end{bmatrix}$$

The combined rotation matrix is given by the product of $R_2$ and $R_1$ as follows:

$$R_C = R_2 \times R_1 = \begin{bmatrix} 4/5 & 3/5 & 0 \\ \frac{3\sqrt{2}}{10} & \frac{2\sqrt{2}}{5} & -\sqrt{2}/2 \\ \frac{3\sqrt{2}}{10} & \frac{2\sqrt{2}}{5} & \sqrt{2}/2 \end{bmatrix}$$

The result of applying $R_2$ to $B'_1$ is:

$B''_1 = [0,0,2\sqrt{5}]$

The transformation matrix $T_C$ is then obtained from $R_C$ by dropping the third row of $R_C$:

$$T_{C1} = \begin{bmatrix} 4/5 & -3/5 & 0 \\ \frac{3\sqrt{2}}{10} & \frac{2\sqrt{2}}{5} & \frac{-\sqrt{2}}{2} \end{bmatrix}.$$

Note that for N Principal Components and M background constituents to be suppressed, the final transformation matrix will have dimensions (N–M, N). Applying $T_C$ to the agent and background Principal Component vectors yields:

$$T_{C1} \times B_1 = \begin{bmatrix} 0 \\ 0 \end{bmatrix}$$

$$T_{C1} \times A_1 = \begin{bmatrix} 4/5 \\ \frac{-7\sqrt{2}}{10} \end{bmatrix}$$

$$T_{C1} \times A_2 = \begin{bmatrix} -2/5 \\ \frac{11\sqrt{2}}{10} \end{bmatrix}$$

The background constituent has been completely suppressed by this transformation, and the two agent Principal Component vectors have been rotated into a new two-dimensional space and comprise the agent library to be used for detection. Note that the rotation matrices and thus the transformation matrices are independent of the magnitude of the background vector and depend only on the direction of the background vector. Thus, the library of background constituents may be normalized to unity, or to any other value, or may be used without normalization.

The teachings of the following publications are herein incorporated by reference:

D. Manolakis, D. Marden, and G. A. Shaw, "Hyperspectral Image Processing for Automatic Target Detection Applications," Lincoln Laboratory Journal 14 (2003) p. 79.

N. Keshava, "A Survey of Spectral Unmixing Algorithms," Lincoln Laboratory Journal 14 (2003) p. 55.

C. A. Primmerman, "Detection of Biological Agents," Lincoln Laboratory Journal 12 (2000) p. 3.

T. H. Jeys, "Aerosol Triggers," New England Bioterrorism Preparedness Workshop (3-4 Apr. 2002).

J. R. Lakowicz, *Principles of Fluorescence Spectroscopy* (Kluwer, N.Y.) 1999.

M. A. Sharaf, D. L. Illman, and B. R. Kowalski, *Chemometrics* (Wiley & Sons, New York) 1986.

*Applied Optics*, "Laser-Induced Breakdown Spectroscopy," (feature issue) 20 Oct. 2003.

*Existing and Potential Standoff Explosives Detection Techniques*, National Research Council (The National Academies Press, Washington D.C.) 2004.

L. S. Powers and C. R. Lloyd, "Method and Apparatus for Detecting the Presence of Microbes and Determining their Physiological Status," U.S. Pat. No. 6,750,006, Jun. 15, 2004.

L. S. Powers, "Method and apparatus for sensing the presence of microbes," U.S. Pat. No. 5,968,766, Oct. 19, 1999.

L. S. Powers, "Method and apparatus for sensing the presence of microbes," U.S. Pat. No. 5,760,406, Jun. 2, 1998.

T. H. Jeys and A. Sanchez, "Bio-particle fluorescence detector," U.S. Pat. No. 6,194,731, Feb. 27, 2001.

Those having ordinary skill in the art will appreciate that various modifications can be made to the above embodiments without departing from the scope of the invention.

The invention claimed is:

1. A method of detecting an agent in a bulk sample including at least one background constituent, comprising:
   utilizing a measurement modality to interrogate the sample with electromagnetic radiation so as to generate spectral data corresponding thereto,
   deriving principal components of the sample spectral data,
   applying a rotate-and-suppress transformation to said principal components of the sample data, wherein said transformation suppresses a contribution of at least one background constituent, if present, and
   comparing said transformed principal components of the sample data with background-suppressed principal components of corresponding spectral data of an agent to determine whether said agent is present in the bulk sample.

2. The method of claim 1, further comprising
   utilizing said measurement modality to obtain spectral data corresponding to the agent,
   deriving principal components of the agent spectral data, and
   applying said rotate-and-suppress transformation to said principal components of the agent data to generate said background-suppressed principal components of the agent data.

3. The method of claim 1, wherein the step of deriving principal components of sample spectral data comprises utilizing Principal Component Analysis (PCA).

4. The method of claim 1, wherein said comparing step comprises determining whether a spectral angle between a vector representing the background-suppressed principal components of the sample data and a vector representing the background-suppressed principal components of the agent data lies within a pre-defined range.

5. The method of claim 4, further comprising indicating detection of the agent in the bulk sample when said spectral angle lies within said range.

6. The method of claim 4, further comprising indicating detection of the agent in the bulk sample when said spectral angle lies with said range and a dot product of said vectors exceeds a predefined threshold.

7. The method of claim 1, further comprising:
   utilizing said measurement modality to obtain spectral data for at least one background constituent,
   deriving principal components of said background spectral data, and
   generating said rotate-and-suppress transformation based on said background principal components of the background constituent data.

8. The method of claim 1, wherein said measurement modality comprises any of fluorescence excitation-emission spectroscopy, fluorescence lifetime spectroscopy, laser-induced breakdown spectroscopy, Raman spectroscopy, Terahertz transmission or reflection spectroscopy, and X-ray fluorerscence.

9. The method of claim 1, wherein said sample comprises a bio-aeosol.

10. The method of claim 1, wherein said sample comprises any of a biowarfare agent, a chemical warfare agent, a radiological agent, an explosive agent, or a pollutant agent.

11. The method of claim 1, wherein said radiation comprises ultraviolet radiation and said measurement modality comprises fluorescence spectroscopy.

12. A method of processing spectral data taken from a sample, comprising
   utilizing a plurality of measurement modalities to interrogate the sample with electromagnetic radiation so as to generate a plurality of sets of spectral data each corresponding to one of said modalities,
   combining the plurality of sets of spectral data into a composite feature vector, and
   transforming said composite feature vector into a single principal component vector.

13. The method of claim 12, wherein said combining step further comprises applying a normalization factor to at least one of said spectral data sets.

14. A method of detecting an agent in a bulk sample including at least one background constituent, comprising:
   utilizing a plurality of measurement modalities to interrogate the sample with electromagnetic radiation so as to generate a plurality of sets of spectral data each corresponding to one of said modalities,
   combining the plurality of sets of spectral data into a composite feature vector,
   transforming said feature vector into a principal component vector,
   applying a rotate-and-suppress transformation to said principal component vector, wherein said transformation suppresses a contribution of said background constituent, if present, to said vector, and
   comparing said transformed principal component vector with a respective background-suppressed agent vector to determine whether said agent is present in the bulk sample.

15. The method of claim 14, wherein said combining step further comprises applying a normalization factor to at least one of said two spectral data sets.

16. The method of claim 14, wherein one of said data sets comprises fluorescence emission-excitation data and the other data set comprises fluorescence lifetime data.

17. The method of claim 16, wherein each fluorescence lifetime datum is normalized utilizing the amplitude of the emission-excitation space at which it was measured.

18. A system for detecting an agent in a bulk sample having at least one background constituent, comprising:
   a background library for storing data corresponding to at least one background constituent,
   an agent library for storing principal components of measurement data corresponding to said agent,
   a preprocessing module in communication with said libraries and adapted to receive measurement data corresponding to a test sample, said module calculating a rotate and suppress transformation and applying said rotate-and-suppress transformation to measurement data corresponding to said test sample so as to generate transformed principal component vectors corresponding to the test sample, wherein said transformation suppresses said background constituent, if present in the test sample, said preprocessing module further applying said transformation to the agent so as to generate background-suppressed principal component vectors corresponding to the agent, and an agent detection module in communication with said preprocessing module to receive said transformed principal component vectors corresponding to the agent and the sample, said agent detection module comparing said vectors to determine whether said agent is present in the sample.

* * * * *